(12) United States Patent
Choudhury et al.

(10) Patent No.: US 9,910,014 B2
(45) Date of Patent: Mar. 6, 2018

(54) METHODS AND SYSTEMS FOR DETECTING GAS FLOW BY PHOTOACOUSTIC SIGNAL GENERATION

(71) Applicant: GENERAL ELECTRIC COMPANY, Schenectady, NY (US)

(72) Inventors: Niloy Choudhury, Glenville, NY (US); William Albert Challener, Glenville, NY (US)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 182 days.

(21) Appl. No.: 14/977,820

(22) Filed: Dec. 22, 2015

(65) Prior Publication Data
US 2017/0176489 A1 Jun. 22, 2017

(51) Int. Cl.
*G01M 3/04* (2006.01)
*G01N 21/17* (2006.01)
(Continued)

(52) U.S. Cl.
CPC .............. *G01N 29/02* (2013.01); *G01M 3/24* (2013.01); *G01M 3/243* (2013.01); *G01M 3/38* (2013.01);
(Continued)

(58) Field of Classification Search
CPC ....... G01N 21/1702; G01N 2021/1704; G01N 2021/1708; G01N 21/17; G02B 6/02304;
(Continued)

(56) References Cited

U.S. PATENT DOCUMENTS 6,089,076 A * 7/2000 Mueller .................. G01M 3/38
250/339.01
7,343,074 B1 * 3/2008 Gallagher .......... G01N 21/3504
250/227.11
(Continued)

FOREIGN PATENT DOCUMENTS

CN 102243128 B 9/2013
EP 1 460 407 A1 9/2004
WO WO 03056313 A1 * 7/2003 ......... G01N 21/7703

OTHER PUBLICATIONS

"Fourier-transform infrared spectroscopy," last edited on Sep. 12, 2017, Retrieved from the Internet URL: https://ewikipedia.org/wiki/Fourier-transform_infrared_spectroscopy, on Sep. 20, 2017, pp. 9.
(Continued)

*Primary Examiner* — R. A. Smith
*Assistant Examiner* — Herbert K Roberts
(74) *Attorney, Agent, or Firm* — Nitin N. Joshi

(57) ABSTRACT

A method for the detection of a gas flowing from a location in a structure is described. A hollow-core optical fiber is placed in a position adjacent the structure. The fiber includes a sound-conductive cladding layer; and further includes at least one aperture extending into its cross-sectional diameter. A beam of pulsed, optical is transmitted into the fiber with a tunable laser. The optical energy is characterized by a wavelength that can be absorbed by the gas that flows into the fiber through the aperture. This causes a temperature fluctuation in the region of gas absorption, which in turn generates an acoustic wave in the absorption region. The acoustic wave travels through the cladding layer, and can be detected with a microphone, so as to provide the location of gas flow, based on the recorded position and movement of the acoustic wave. A related system is also described.

20 Claims, 4 Drawing Sheets

(51) Int. Cl.
*G02B 6/02* (2006.01)
*G02B 6/032* (2006.01)
*G01N 29/02* (2006.01)
*G01M 3/38* (2006.01)
*G01M 3/24* (2006.01)
*G01N 29/024* (2006.01)
*G01N 29/14* (2006.01)
*G01N 29/24* (2006.01)

(52) U.S. Cl.
CPC ......... *G01N 21/17* (2013.01); *G01N 21/1702* (2013.01); *G01N 29/024* (2013.01); *G01N 29/14* (2013.01); *G01N 29/2418* (2013.01); *G02B 6/02304* (2013.01); *G02B 6/02328* (2013.01); *G02B 6/02366* (2013.01); *G01N 2021/1704* (2013.01); *G01N 2021/1708* (2013.01); *G01N 2291/012* (2013.01); *G01N 2291/021* (2013.01)

(58) Field of Classification Search
CPC .. G02B 6/02328; G02B 6/02366; G01M 3/38
See application file for complete search history.

(56) References Cited

U.S. PATENT DOCUMENTS

| | | | |
|---|---|---|---|
| 8,133,593 B2* | 3/2012 | Carberry | G01N 21/05 385/123 |
| 8,193,496 B2 | 6/2012 | Furry | |
| 2008/0180675 A1 | 7/2008 | Sheen et al. | |
| 2010/0064777 A1 | 3/2010 | Howieson | |
| 2016/0356700 A1* | 12/2016 | Rouxel | G01N 29/2418 |
| 2017/0097464 A1* | 4/2017 | Challener | G02B 6/02309 |

OTHER PUBLICATIONS

"Gas-Liquid Chromatography," last modified on Jul. 2016, Retrieved from the Internet URL:http://www.chemguide.co.uk/analysisichromatography/gas.html, on Sep. 20, 2017, pp. 7.

Argyros, A., et al., "Hollow-Core Microstructured Polymer Optical Fiber," Optics Letters, vol. 31, No. 2, pp. 172-174 (Jan. 15, 2006) (Abstract).

Besson, J.P., et al., "Multi-gas sensing based on photoacoustic spectroscopy using tunable laser diodes," Spectrochimica Acta Part A: Molecular and Biomolecular Spectroscopy, vol. 60, Issue 14, pp. 3449-3456 (Dec. 2004).

Chen, R., "Photoacoustic photonic crystal fiber gas sensor," Massachusetts Institute of Technology. Dept. of Electrical Engineering and Computer Science, pp. 1-93 (Feb. 2, 2007).

Chou, J., "Infrared Gas Sensors," in Hazardous gas monitors, McGraw-Hill Book Company, Chapter 5, pp. 55-72 (2000).

Eltschlager, K.K., et al., "Technical measures for the investigation and mitigation of fugitive methane hazards in areas of coal mining," Office of Surface Mining Reclamation and Enforcement, pp. 1-129 (Sep. 2001).

Ho, C.K., et al., "Review of Chemical Sensors for In-Situ Monitoring of Volatile Contaminants," Sandia National Laboratories, pp. 1-34 (Mar. 2001).

Huang, E., et al., "High-sensitivity photoacoustic leak testing," The Journal of the Acoustical Society of America, vol. 114, Issue 4, Part 1, pp. 1926-1933 (Oct. 2003).

Kauppinen, J., et al., "High sensitivity in gas analysis with photoacoustic detection," Microchemical Journal, vol. 76, Issues 1-2, pp. 151-159 (Feb. 2004).

Kissell, F.N., "Handbook for methane control in mining," National Institute for Occupational Safety and Health, Pittsburgh Research Laboratory, pp. 1-184 (2006).

Lackner, M., et al., "Demonstration of methane spectroscopy using a vertical-cavity surface-emitting laser at 1.68 μm with up to 5 MHz repetition rate," Measurement Science and Technology, vol. 14, No. 1, pp. 101-106 (2003).

Lewis, J. and Schrier, P., "Low self noise: The first step to high-performance MEMS microphone applications," EE Times, dated Nov. 28, 2012, Retrieved from the Internet URL: http://www.eetimes.com/document.asp?doc_id=1280170, EE Times, pp. 4.

Meng, J., et al., "Investigation on an evanescent wave fiberoptic absorption sensor based on fiber loop cavity ring-lown spectroscopy," Optics Communications, vol. 283, Issue 2, pp. 249-253 (Jan. 15, 2010).

Miklós, A., et al., "Photoacoustic Spectroscopy, Theory," Encyclopaedia of Spectroscopy and Spectrometry, pp. 1815-1822 (Dec. 1999).

Morville, J., et al., "Two schemes for trace detection using cavity ringdown spectroscopy," Applied Physics B: Lasers and Optics, vol. 78, Issue 3-4, pp. 465-476 (Feb. 2004).

Otagawa, T., et al., "A room-temperature electrochemical sensor and instrument for monitoring methane," Sensors and Actuators, vol. 8, Issue 1, pp. 65-88 (Sep. 1985).

Rieker, G.B., "Wavelength-modulation spectroscopy for measurements of gas temperature and concentration in harsh environments," Dissertation submitted to Department of Mechanical Engineering, Stanford University, pp. 1-163 (May, 2009).

Rollick, K., et al. "Combustible gas detector sensor drift: Catalytic vs. infrared," MSA The Safety Company, ID 07-0035-MC, pp. 1-2 (Aug. 2011).

Schäfer, S., et al., "Sensitive detection of methane with a 1.65 μm diode laser by photoacoustic and absorption spectroscopy," Applied Physics B: Lasers and Optics, vol. 66, Issue 4, pp. 511-516 (Apr. 1998).

Tam, A.C., "Applications of photoacoustic sensing techniques," Review of Modern Physics, Issue 58, pp. 381-431 (Apr. 1, 1986).

Waechter, H., et al., "Chemical sensing using fiber cavity ring-down spectroscopy," Sensors, vol. 10, Issue 3, pp. 1716-1742 (Mar. 2010).

Wang, W., et al., "A room temperature SAW based methane gas sensors," IEEE International Ultrasonics Symposium, pp. 2148-2150 (Jul. 21-25, 2013).

Wang, Z., et al., "Methane-oxygen electrochemical coupling in an ionic liquid: A robust sensor for simultaneous quantification," Analyst, vol. 139, Issue 20, pp. 5140-5147 (Aug. 2014).

Weston, D.E., "The Theory of the Propagation of Plane Sound Waves in Tubes," Proceedings of the Physical Society, Section B, vol. 66, No. 8, pp. 695-709 (1953).

Yönak, S.H., and Rowling, D.R., "Parametric dependencies for photoacoustic leak localization," The Journal of the Acoustical Society of America, vol. 112, Issue 1, pp. 145-155 (Jul. 2002).

* cited by examiner

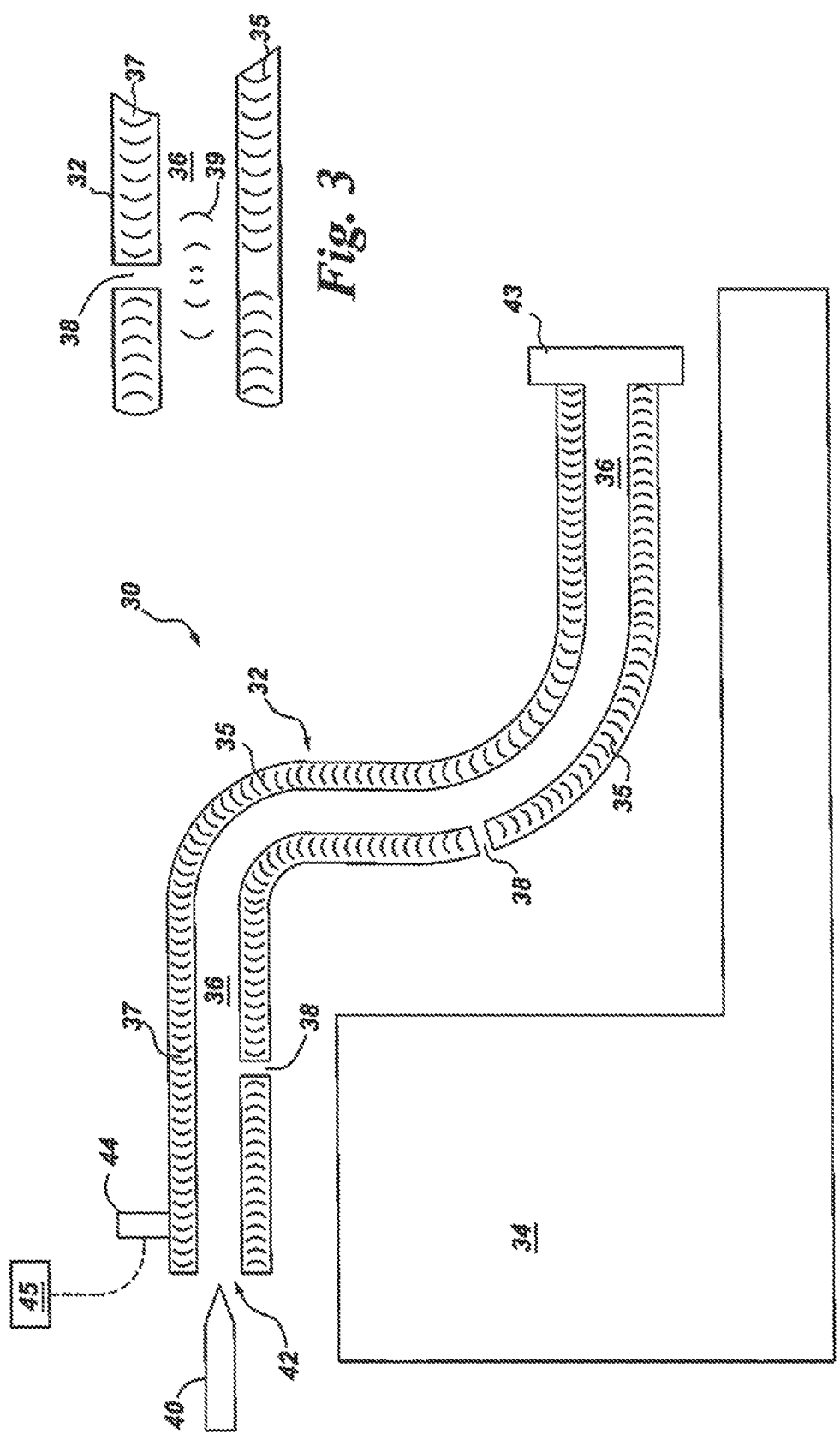

METHODS AND SYSTEMS FOR DETECTING GAS FLOW BY PHOTOACOUSTIC SIGNAL GENERATION

STATEMENT REGARDING FEDERALLY SPONSORED RESEARCH & DEVELOPMENT

This invention was made with Government support under award number DE-AR0000543, awarded by the Advanced Research Projects Agency-Energy (ARPA-E). The Government has certain rights in the invention.

TECHNICAL FIELD

This disclosure relates to the detection of gas compositions. In some particular embodiments, the invention relates to methods for detecting gas leaks in fuel pipelines and other structures.

BACKGROUND OF THE INVENTION

Gas detection is a critical capability in many industries that handle or produce chemicals and various gaseous materials. In particular, greater demands in the technology of gas leak detection have arisen for a number of reasons, including industrial efficiency, health and safety considerations, and environmental regulations. Gas detectors are widely used in many environments—industrial plants, refineries, wastewater treatment facilities, vehicles, and homes, to name just a few. Carbon dioxide, carbon monoxide, methane, butane, and hydrogen sulfide are some of the gasses that often require detection and/or monitoring.

Many prior art systems and techniques are available for different types of gas detection. Examples include photo-ionization; flame ionization; photoacoustic techniques; infra-red (IR) absorption; open-path gas cell IR-sensing; electrochemical sensing; gas chromatography; and a wide range of spectroscopic techniques. Some examples of the spectroscopic class are laser absorption spectroscopy, wavelength modulation absorption spectroscopy; cavity ring-down spectroscopy (CRDS), and fourier transform infrared spectroscopy; as well as spectroscopic versions of the above-mentioned photoacoustic techniques.

Many of the techniques mentioned above are useful in various situations that involve gas detection. However, most of them also present some disadvantages in practice. For example, the open path gas cell IR sensors are widely used for gas monitoring. While useful in some situations, gas detection is localized in these systems, and a distributed sensing network would require multiple gas cells. Also, the optical components in the gas cells require very accurate alignment, and this can result in high system cost. Moreover, standard laser absorption spectroscopy techniques such as TDLAS can advantageously detect very low concentrations of selected gasses, but they also require complicated drive electronics and expensive system components. Additionally, integration of TDLAS into a distributed sensing network can be complicated, and can lead to a bulky system.

Potentiometric and amperometric sensing techniques are usually solid state-based, and involve the use of an electrolytic liquid or gel in which two identical electrodes are incorporated. A gas sample being analyzed passes through an associated membrane, and oxidizes or becomes reduced at one of the electrodes, based on the composition of the sample. The electrical potential or current is measured across the electrodes, to determine the quantity of the gas.

While these types of techniques may be specifically effective for accurately analyzing multi-gas mixtures, they also appear to have some drawbacks. For example, the types of gasses that can be analyzed with these techniques may be limited. Also, the techniques may not be able to discriminate between different types of organic compounds. Moreover, membranes that are a necessary component are prone to damage; and frequent calibration of such a system may be required. Furthermore, the potentiometric/amperometric nature of these techniques requires a number of electrical connections, and may also require remote monitoring. This would probably necessitate the use of power-consuming wireless systems, adding to the overall cost of the system.

With these concerns in mind, new gas detection systems would be welcome in the art. The new systems should be able to both detect a gas species of interest, and to accurately determine its location, e.g., with good sensitivity. The systems should also be relatively simple in design, and faster than systems such as gas chromatography. These advanced detection systems should also allow for easy placement near a gas source, e.g., without requiring critical optical alignment, which is often required for cavity techniques like CRDS. The new detection systems should also be relatively economical, in terms of both set-up and operation.

BRIEF DESCRIPTION OF INVENTION EMBODIMENTS

One embodiment of the invention is directed to a method for the detection of a gas flowing from a location in a structure, comprising the steps of a) providing a hollow-core optical fiber in a position adjacent the structure; wherein the fiber includes a sound-conductive cladding layer; and further includes at least one aperture extending into its cross-sectional diameter;

b) transmitting a beam of pulsed, optical energy into the fiber with a tunable laser, wherein the optical energy is characterized by a wavelength that can be absorbed by the gas that flows into the fiber through the aperture, thereby causing a temperature fluctuation in the region of gas absorption, which in turn generates an acoustic wave in the absorption region, said acoustic wave travelling through the cladding layer; and c) detecting the acoustic wave with a detection means that can provide the specific location of gas flow, based on the recorded position and movement of the acoustic wave.

Another embodiment of the invention is directed to a system for the detection of a gas flowing from a location in a structure. The system includes:

(i) a hollow-core optical fiber in a position adjacent the structure, wherein the fiber includes a sound-conductive cladding layer; and further includes at least one aperture extending into its cross-sectional diameter;

(ii) a tunable laser configured to transmit a beam of pulsed, optical energy through a central core region of the fiber; wherein the optical energy is characterized by a wavelength that can be absorbed by the gas that flows into the fiber through the aperture; thereby causing a temperature fluctuation in the region of gas absorption, which in turn generates an acoustic wave in the absorption region, said acoustic wave travelling through the cladding layer; and (iii) means for detecting the acoustic wave and providing a location of the gas flow, based on the recorded position and movement of the acoustic wave.

BRIEF DESCRIPTION OF THE DRAWINGS

FIG. 2 is a schematic diagram of a gas detection system according to embodiments of this invention.

FIG. 3 is a cross-section of a portion of the hollow core fiber of FIG. 2.

DETAILED DESCRIPTION

Figure 1:
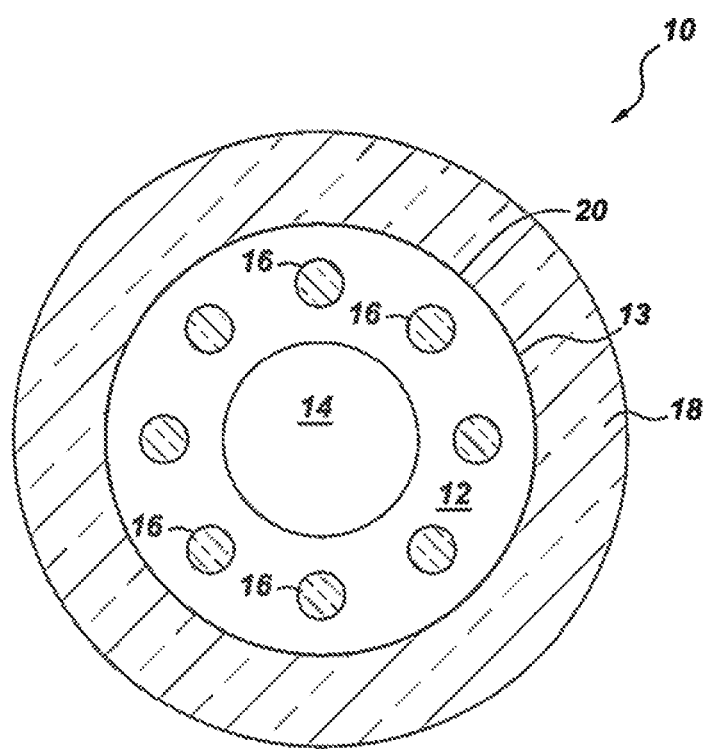
FIG. 1 is a cross-sectional, end-view perspective of a hollow core fiber.

Approximating language, as used herein throughout the specification and claims, may be applied to modify any quantitative representation that could permissibly vary without resulting in a change in the basic function to which it is related. Accordingly, a value modified by a term or terms, such as "about", and "substantially" is not to be limited to the precise value specified. In some instances, the approximating language may correspond to the precision of an instrument for measuring the value. Here and throughout the specification and claims, range limitations may be combined and/or interchanged. Such ranges are identified and include all the sub-ranges contained therein, unless context or language indicates otherwise.

In the following specification and claims, the singular forms "a", "an" and "the" include plural referents unless the context clearly dictates otherwise. As used herein, the term "or" is not meant to be exclusive; and refers to at least one of the referenced components being present; and includes instances in which a combination of the referenced components may be present, unless the context clearly dictates otherwise.

Embodiments of the method claimed herein detect gas flowing from a location (or multiple locations) of a structure. As used herein, the term "structure" may refer to a wide variety of objects, including commercial buildings, homes, vehicles, waste-water treatment plants, chemical plants, power plants, and many other types of factories. In some specific embodiments, the structure can be one or more features of an oil drilling operation or any type of oil rig. Non-limiting examples include the oil pad or oil drilling platform, as well as an oil pipeline, e.g., one that runs from an oil well to a seaport or other type of collection site. Methane gas leaks from an oil pad or pipeline often represent a serious problem for a number of reasons, as noted previously.

A hollow-core optical fiber is put into position adjacent the structure from which gas may be leaking. This type of fiber is generally known in the art, and is capable of guiding light through its hollow, inner region. An advantage of such a fiber is that it allows transmission of long wavelength light (e.g., greater than about 2 microns), which is more strongly absorbed by the silica glass. The fiber can provide a high damage threshold—even with a high-energy light beam. One commercial source for hollow core optical fibers that can be used for this invention is Thorlabs Inc., Newton, N.J. Many references generally describe these types of fibers, such as "Hollow-Core Microstructured Polymer Optical Fiber", by A. Argyros et al, Optics Letters, Vol. 31, No. 2/Jan. 15, 2006.

Many fibers of this type are made by drawing glass (silica) or a plastic to a desired diameter—often slightly thicker than a human hair. In some cases, the inner diameter of the hollow-core fiber (i.e., the cross-sectional size of the hollow region) will be in the range of about 10 microns to about 75 microns. The hollow region is sometimes referred to as a "transparent core". Light can be channeled through the core by way of internal reflection, and this can allow the fiber to function as a waveguide. (Those skilled in the art understand that there are other ways of confining light to the core).

For embodiments of the present invention, the optical fiber is surrounded by at least one cladding layer, surrounding the external surface of the fiber wall. In the case of a glass fiber, the cladding layer itself is usually formed of some type of glass. As described below, the cladding layer functions to propagate an acoustic wave generated in the process. The thickness of the cladding wave can vary considerably, and is based on a number of factors, such as the overall diameter of the hollow core fiber; its composition; and the type of optical energy being transmitted through the hollow core.

The optical fiber that is useful herein is often referred to as "microstructured optical fiber". This type of material includes at least one layer containing a pattern of porous regions (often air-filled), surrounding a hollow core. The surrounding layer often comprises various arrangements of silica filaments.

FIG. 1 is an end-view perspective of a hollow core fiber 10, in cross-section, suitable for some embodiments of this invention. Fiber 10 includes an inner cladding layer 12 within wall 13, formed of glass. The inner cladding layer 12 surrounds a hollow core region 14, discussed below. Layer 12 can itself include hollow space, or it can be filled or partially filled with glass, or other types of insulation.

In some embodiments, inner cladding layer 12 also includes a group of spaced glass tubes 16, generally concentric along the length of fiber 10 (i.e., concentric with a longitudinal dimension of the hollow central region). These tubes are often hollow as well, although they may be solid, or partially filled. The size and number of glass tubes 16 can vary significantly. For example, in some cases, there may be less than ten glass tubes 16; while in other cases, inner cladding layer 12 could be completely filled with the glass tubes, which would form a honeycomb that surrounds hollow core region 14. The number, size, arrangement, and specific composition of glass tubes 16 will depend on a variety of photonic characteristics and factors. The primary purpose of these interior glass tubes is to controllably confine and direct pulsed optical energy through hollow core region 14.

With continued reference to FIG. 1, fiber 10 includes at least one sound-conductive outer cladding layer 18, sometimes referred to as an "outer shell". In most embodiments, the outer cladding layer concentrically surrounds the external surface 20 of wall 13, i.e., surrounding the inner cladding layer. Usually, the cladding layer is also formed of a silica material like glass. However, it need not be the same composition or microstructure as any other type of glass in the fiber structure, e.g., the material that may be filling layer 12. In some specific embodiments, the outer cladding layer is formed of a solid glass material.

One of the key requirements for the outer cladding layer is that it have a diameter and composition sufficient to propagate an acoustic wave generated by the action of the laser beam, as further described below. Those skilled in the art understand that there are many ways to form the cladding layer (i.e., both layers 12 and 18), e.g., by way of coating techniques or vapor deposition processes. Often, the cladding layer is extruded along with the primary, central region of the fiber, during fabrication; and other fabrication steps are usually involved as well.

FIG. 2 is a schematic diagram of a gas detection system 30, according to embodiments of this invention. A hollow core fiber 32 is positioned adjacent a structure 34. As explained earlier, the structure, shown in simplistic form, can take on a wide variety of forms. In some specific embodiments, the structure is one or more components associated with an oil drilling operation, e.g., a pipeline or oil pad. The average distance between structure 34 and hollow core fiber 32 will depend on a variety of factors, including the characteristics of the gas being detected, e.g., its vapor pressure and density; the amount of gas that is expected to flow (e.g., leak) from the structure; the sensitivity of the detection system; and the accessibility of the detection system to the structure.

Hollow-core fiber 32 (FIG. 2) is meant to have features similar to the fiber described in FIG. 1, although not all of them are depicted in this figure, for the sake of simplicity. Thus, in many embodiments, cladding layer 37 would actually comprise an inner cladding layer and an outer cladding layer, surrounding central region 36. The inner cladding layer would typically include a group of glass tubes in some pattern, as in FIG. 1. Moreover, although fiber 32 is depicted as curved, that shape may not necessarily be in place. Generally, the fiber would be aligned with the general contour of a surface of structure 34, i.e., a surface from which gas would flow.

With continued reference to FIG. 2, the hollow core fiber includes at least one side-hole or aperture 38 that extends through the fiber wall (i.e., through both cladding layers, when present) and into the central core region 36 of the fiber. Multiple apertures 38 are usually present, as in the figure, spaced from each other. These apertures allow the flow of gas from the structure into the interior region of the fiber. As an example, leaking gas from a structure such as an oil pipeline would flow into the fiber via one or more apertures closest to the pipeline leak.

The size of the apertures, as well as their number and spacing, will depend on various factors, some of which were mentioned above in regard to other process considerations. The factors include: the amount of gas flowing out of the structure, or expected to flow out of the structure; and the identity of the gas and its properties.

A general, non-limiting estimate can be provided for a commercial oil pipeline that might be leaking hydrocarbon gases such as methane. In such a case, a hollow core fiber having an overall diameter of about 250 microns to about 750 microns could be situated next to the pipeline. Such a fiber may include about 100 holes for every 10 meters of length, but this number can vary considerably. The holes could be situated around the entire outside surface of the fiber, but in some cases, would be present only on surfaces generally facing the pipeline. Each hole might have a diameter in the range of about 10 microns to about 50 microns.

As mentioned above, the process includes the step of transmitting a beam of optical energy into the fiber. The optical energy can be in pulsed form, or can be sinusoidally modulated at a given frequency. In most embodiments, a tunable laser 40 (FIG. 2) is employed to provide the light pulse/modulation, through one end 42 of the fiber. The other end of the fiber sometimes terminates at a light collection window 43, although the fiber could be open-ended as well. The type of laser can vary considerably, as long as it is capable of producing a wavelength that matches an absorption spectrum band of the gas being detected in the process, and is capable of operating in a pulsed mode, as described below. Examples of suitable lasers include a pulsed laser, modulated laser, carbon dioxide ($CO_2$) laser, an ultraviolet (UV) laser, excimer laser, helium cadmium (HeCd) laser, solid state laser, diode laser, ion laser, fiber laser, helium neon laser, and a DFB diode laser ("distributed feedback laser", or sometimes referred to as a "distributed Bragg reflector laser").

As those skilled in the art of absorption spectroscopy understand, gases are characterized by at least one absorption peak across the electromagnetic spectrum. Thus, the precise identity of absorption bands for gases like water vapor and a variety of common alkane chemicals (e.g., methane, ethane, butane, and hexane) are all available, and can be used as reference points for this process. (One source for such information is the HITRAN spectroscopic database). Also, U.S. Pat. No. 8,193,496 (D. Furry), provides an illustration of absorption values for various hydrocarbons, and is incorporated herein by reference. In the case of methane, the absorption peaks that are typically used for these inventive embodiments are at wavelengths of 1.6 microns, 2.4 microns, 3.2 microns, and 7.7 microns.

The present inventors discovered that the phenomenon of photoacoustic signal generation could be used with the hollow core fiber to detect and localize a chemical gas leak, or to detect any gas flowing from a structure. The photoacoustic effect, sometimes referred to as the "optoacoustic effect", is the formation of sound waves following light absorption in a material—here, a gas material. The photoacoustic effect can be considered a form of laser spectroscopy, and is capable of very high sensitivity for gas detection.

As noted above, the photoacoustic effect can be quantified through the absorption of a modulated laser beam by the gas species of interest, with the subsequent generation of acoustic waves at the modulation frequency. In other words, if the modulation frequency of the light source is in the acoustic range, e.g., from about 10 Hz-20,000 Hz, then the resulting pressure wave is an acoustic wave. As further described below, the amplitude of the acoustic signal can be measured by a microphone or piezoelectric device. The strength of the pressure wave P is directly proportional to the total absorbed energy, H, according to the following equation:

$$P_{max} \propto H = I_0 \Delta t \alpha = I_0 \Delta t \alpha c \qquad (1),$$

where $I_0$ is the incident light intensity, $\Delta t$ is the pulse-width of the light pulse, and $\alpha$ is the absorption coefficient of the specimen. The absorption coefficient, $\alpha$, is the product of absorptivity, $\alpha$, and concentration, c. The value $\alpha$ is wavelength-dependent and therefore, $P_{max}$ will also be wavelength-dependent. From equation 1, it also follows that by measuring the strength of the acoustic wave, one can determine the concentration, "c" of the gas species.

Techniques are available to further amplify the signal to enhance the monitoring/detection system. A description of the photoacoustic effect and its relevance to gas detection can be found in a paper entitled "Photoacoustic Photonic Crystal Fiber Gas Sensor", by Raymond Chen, published by Massachusetts Institute of Technology (2007). The contents of this document are incorporated herein by reference.

Referring to FIG. 2, tunable laser 40 transmits a pulsed light beam (usually characterized by a modulated intensity), with a pre-selected wavelength through the central region 36 of fiber 32. If the gas species of interest is present, the pulsed light beam will contact the gas and be absorbed by the gas. A temperature fluctuation will occur in the region of gas absorption. The temperature fluctuation, in turn, results in the formation of sound waves.

FIG. 3 depicts a simplified cross-section (lengthwise) of a portion of the hollow core fiber 32 of FIG. 2, showing central region 36 and cladding 37. The present inventors discovered that, in the case of a glass fiber, the acoustic signal, illustrated by sound waves 35, propagates much more effectively through cladding 37, as compared to propagation through the central core region 36. Moreover, in the case of the two-layered cladding, as discussed above, the sound waves propagate especially well through the outer cladding layer, e.g., layer 18 in FIG. 1, which is usually formed of solid glass. (In FIG. 3, the limited degree of sound propagation via sound waves 39 through the hollow central region is also illustrated, in simple form). Experimental observation showed that the amount of energy transferred through the fiber is determined by the acoustic impedances of the glass and the surrounding air, and by the local geometry of the fiber itself In one study involving a planar interface between glass and air, the acoustic energy transferred into the glass was reduced by about 75 dB (decibels). However, once a portion of the acoustic energy entered the glass cladding of the fiber, the cladding functioned as an excellent conductor of sound.

The amplitude of the acoustic signal can be measured by a suitable detection means. In some instances, this can take the form of a microphone. In other cases, a piezoelectric sensor may be employed, e.g., one designed to measure changes in pressure or temperature as the pulsed light beam interacts with the gas that has entered the fiber. These types of sensors are commercially available.

In one embodiment depicted in FIG. 2, a microphone 44 is positioned at one end 42 of fiber 32, and can be bonded or otherwise attached to the fiber. A variety of microphones can be used for this purpose, and most of them measure sound pressure level (SPL), rather than sound energy or intensity. As an example, state-of-the-art MEMS (microelectromechanical system) switches achieve signal-to-noise ratios (SNR) of about 66 dB, resulting in an equivalent input noise of about 28 dB.

In this embodiment, using microphone 44, the relative phase between the modulated light (i.e., the pulsed optical beam) and the detected acoustic signal can be measured. This measurement allows an operator to localize the source of the acoustic signal, as well as its intensity. More specifically, in regard to the detection of gas flow (such as a gas leak), the phase shift of the reflected acoustic signal can be measured with respect to the light source modulation. For example, at 10 Hz, the wavelength of sound is approximately 34 m. Therefore, for 1 m resolution, the phase of the acoustic signal must be determined to within 10 degrees (10°). In most embodiments, at least one standard computer processor 45 is used to process the acoustic signals and perform the other calculations regarding gas location.

Figure 4:
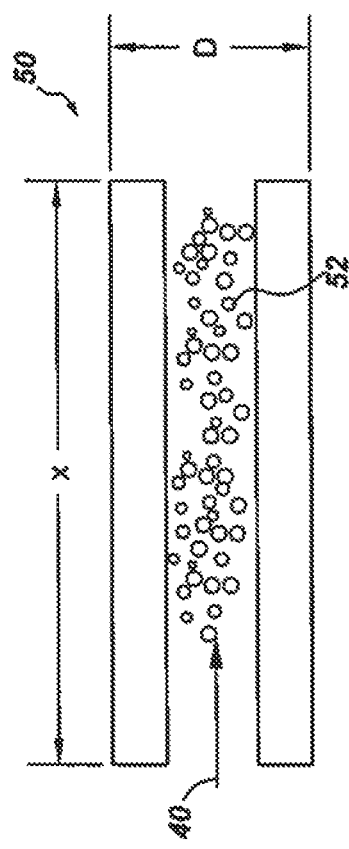
FIG. 4 is another cross-section of a section of a hollow core fiber.

A simulation of photoacoustic generation in a hollow-core fiber was carried out, wherein the gas being detected was methane. Thus, in order to estimate the strength of an acoustic signal that would be generated from methane absorption in the fiber, several assumptions were made. FIG. 4 is a simple depiction of a section of a hollow core fiber 50 that contains methane gas 52. Fiber section 50 has length "x" and an overall diameter "D". The volume of the fiber section is $$V = \frac{\pi D^2}{4} x. \tag{2}$$

If light radiation at 3.24 μm is incident on this section of the fiber, then a percentage of the radiation will get absorbed by the gas (methane), and lead to heating of the gas.

Moreover, if a sinusoidally modulated light intensity passes through the gas, then there will be periodic heating and cooling of the gas. In most cases, since the incident radiation completely fills up the enclosed gas volume within the fiber, the gas cannot isobarically expand immediately after the light pulse deposits energy. Instead there will be a pressure increase, referenced as "$P_0$". This photoacoustic pressure value, $P_0$, can be expressed by Equation 3, below.

$$P_0 = \frac{(\gamma - 1)\alpha \times P}{\omega V} = \frac{2(\gamma - 1)\alpha P}{\pi^2 f D^2}, \tag{3}$$

where γ is the adiabatic coefficient; α is the absorption coefficient of methane at the incident wavelength, P is the incident power; ω=2πf is the angular frequency of light modulation; and f is the frequency of light modulation. Using γ=1.4, α=0.138 m$^{-1}$ (for 69 ppm of methane concentration), P=10 mW, D=50 μm, f=10 Hz, the value for $P_0$ is approximately 4475 Pa. The threshold of audible sound pressure is $P_{th}$=20×10$^{-6}$ Pa, so $P_0$ expressed in dB is $S_{pl}$=20 log($P_0/P_{th}$)=167 dB.

As the sound propagates through the hollow core of the fiber, it will be strongly attenuated. The amount of attenuation per unit length is inversely proportional to the radius of the core, and directly proportional to the square root of frequency. As noted above, however, it was discovered that acoustic energy transferred to the cladding of the fiber resulted in excellent sound conduction in that region, and this can serve as the basis for effective location of the gas species of interest.

Figure 5:
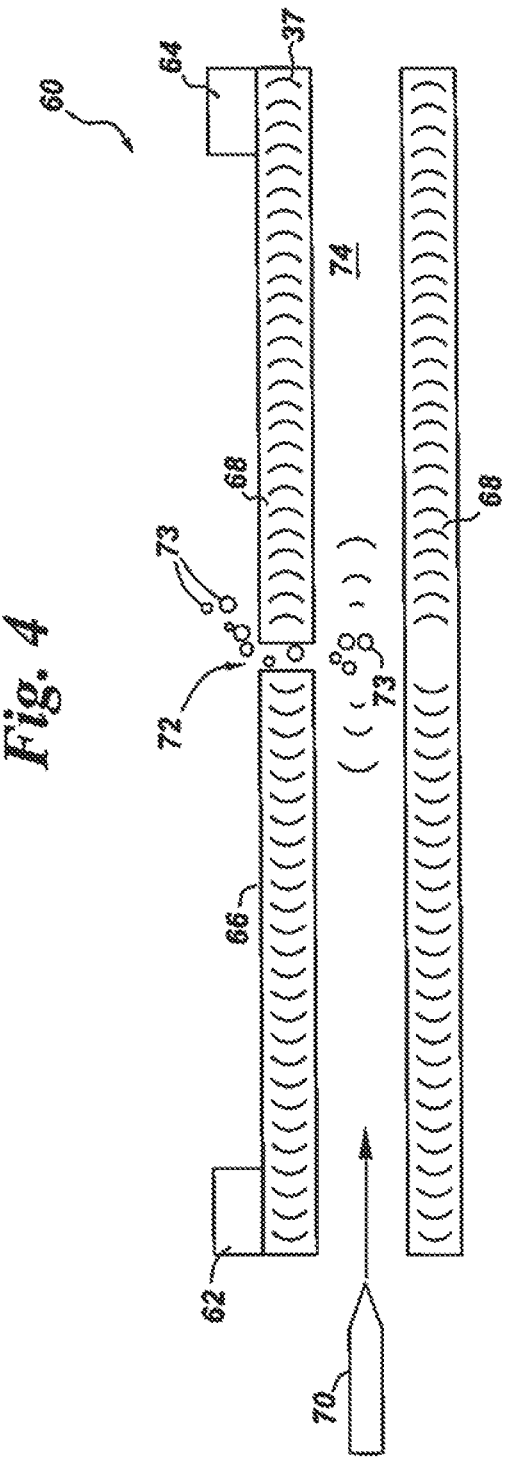
FIG. 5 is a simplified schematic of another hollow-core fiber, in cross-section.

FIG. 5 is a simplified schematic for another embodiment of the invention, showing hollow core fiber 60. Here, two microphones 62 and 64 are employed, attached to an outside surface 66 of the glass cladding 68 of the fiber. Each microphone is usually (though not always) located at a respective end of the fiber. As in previous embodiments, a tunable laser (not shown) is usually the source of a modulated laser beam 70. A gas 73 being detected flows through at least one aperture 72, into the hollow central region 74 of fiber 60. (The internal glass tubes which may also be present within the central region are not shown here, for the sake of simplicity).

As in the other embodiments, the modulated light beam will contact the gas and be absorbed by the gas. A temperature fluctuation will occur in the region of gas absorption. The temperature fluctuation, in turn, results in the formation of sound waves, which are picked up by both microphones 62 and 64. The relative distance of the leak source (i.e., the gas flow) from the two microphones will be determined as a phase difference in the recorded acoustic signal detected by the two microphones. (However, it should be noted that a phase difference may not always be necessary to carry out this technique. For example, in some embodiments, the acoustic signals could be exactly in-phase with each other).

Figure 6:
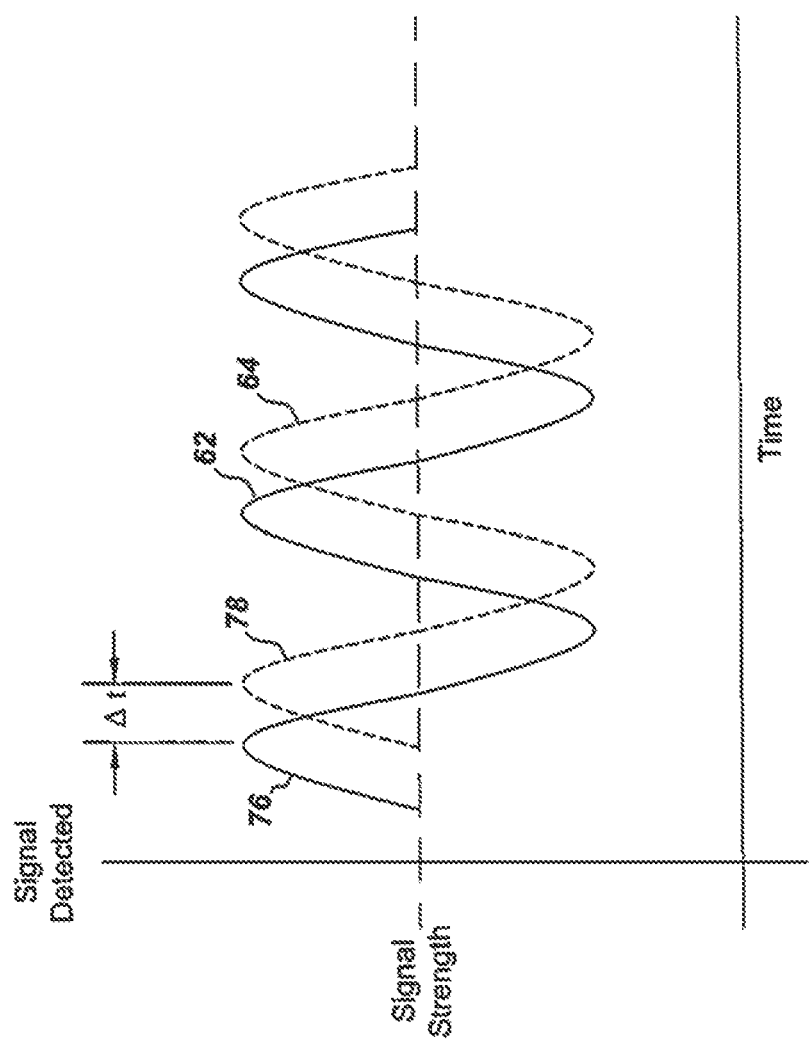
FIG. 6 is a graph plotting acoustical signal data strength as a function of time.

FIG. 6 is a graphical depiction of the signal data from microphones 62 and 64 of FIG. 5, where the Y-axis represents signal strength, while the X-axis represents time. The data from each microphone is usually triggered by the same clock. Sinusoidal curve 76 corresponds to microphone 62, while sinusoidal curve 78 corresponds to microphone 64. The peaks for each sine curve are spaced from each other by the time differential Δt (delta t); and Z represents the length unit. $V_s$ represents the speed of sound within the glass cladding material. The location of the hole, relative to one end of the fiber, can be calculated from the following equation:

$$Z=V_s(\Delta t) \quad (4)$$

(As in other embodiments, a computer processor can be used in the calculation and the evaluation of acoustic signals). The location of the hole is a clear indication of the location of the gas, e.g., the location of a gas leak in a structure adjacent the hollow core fiber, as described previously. Moreover, the use of two microphones may be advantageous in some instances. For example the dual acoustic signals may permit a more precise location for the aperture, e.g., by way of triangulation of the signals. This can in turn lead to more accurately locating a gas leak, as an illustration.

As alluded to previously, it should also be understood that the optical energy transmitted through the fiber can take the form of a pulsed light beam. Thus, in the case of using two microphones, the pulsed light beam would contact a gas that passed into the fiber through one of the apertures, causing a temperature fluctuation and, in turn, a sound pulse. The sound pulse traveling through the fiber is detected by each microphone. Based on the time difference between the microphones, i.e., the time-of-arrival, once can detect the location of the aperture, and consequently, as explained above, the location of the gas of interest.

While only certain features of the invention have been illustrated and described herein, many modifications and changes will occur to those skilled in the art. It is, therefore, to be understood that the appended claims are intended to cover all such modifications and changes as fall within the true spirit of the invention.

What is claimed:

1. A method for the detection of a gas flowing from a location in a structure, comprising the steps of
   a) providing a hollow-core optical fiber in a position adjacent the structure; wherein the fiber includes at least one sound-conductive cladding layer; and further includes at least one aperture extending into its cross-sectional diameter;
   b) transmitting a beam of pulsed, optical energy into the fiber with a tunable laser, wherein the optical energy is characterized by a wavelength that can be absorbed by the gas that flows into the fiber through the aperture, thereby causing a temperature fluctuation in a region of gas absorption, which in turn generates an acoustic wave in the absorption region, said acoustic wave travelling through the cladding layer; and
   c) detecting the acoustic wave with a detection means that can provide the location of gas flow, based on a recorded position and movement of the acoustic wave.

2. The method of claim 1, wherein the fiber includes multiple apertures, spaced from each other.

3. The method of claim 1, wherein the fiber comprises an inner cladding layer surrounding a hollow central region, and an outer cladding layer surrounding the inner cladding layer.

4. The method of claim 3, wherein the inner cladding layer is hollow.

5. The method of claim 4, wherein the inner cladding layer comprises a group of spaced, hollow glass tubes concentric with a longitudinal dimension of the hollow central region.

6. The method of claim 5, wherein the hollow glass tubes are arranged in a pattern that functions to maintain the beam of pulsed, optical energy substantially in the center of the hollow central region of the fiber.

7. The method of claim 3, wherein the outer cladding layer comprises solid glass.

8. The method of claim 7, wherein the strength of the acoustic wave is greatest within the outer cladding layer.

9. The method of claim 1, wherein the tunable laser is selected from a group consisting of a pulsed laser, modulated laser, carbon dioxide ($CO_2$) laser, an ultraviolet (UV) laser, excimer laser, helium cadmium (HeCd) laser, solid state laser, diode laser, ion laser, fiber laser, helium neon laser, and a DFB diode laser.

10. The method of claim 1, wherein the detection means for the acoustic wave comprises a microphone.

11. The method of claim 10, wherein the pulsed optical beam from the laser is characterized by a modulated intensity; and the microphone measures the relative phase between the pulsed optical beam and the detected acoustic wave, to determine a source of the acoustic wave.

12. The method of claim 11, wherein determination of the source of the acoustic wave based on the microphone measurements is carried out by a computer processor.

13. The method of claim 1, wherein the detection means for the acoustic wave comprises two microphones.

14. The method of claim 13, wherein one microphone is located at or near one end of the hollow core optical fiber, and the other microphone is located at or near an opposite end of the fiber.

15. The method of claim 14, wherein the acoustic wave provides a recorded acoustic signal; and wherein each microphone detects the acoustic signal; and a relative distance to the location of gas flow is determined by way of a phase difference in the recorded acoustic signal between the two microphones.

16. The method of claim 1, wherein the structure is an oil drilling pad, oil drilling platform, or an oil pipeline.

17. A system for the detection of a gas flowing from a location in a structure, comprising
   (i) a hollow-core optical fiber in a position adjacent the structure, wherein the fiber includes a sound-conductive cladding layer; and further includes at least one aperture extending into its cross-sectional diameter;
   (ii) a tunable laser configured to transmit a beam of pulsed, optical energy through a central core region of the fiber; wherein the optical energy is characterized by a wavelength that can be absorbed by the gas that flows into the fiber through the aperture; thereby causing a temperature fluctuation in a region of gas absorption, which in turn generates an acoustic wave in the absorption region, said acoustic wave travelling through the cladding layer; and
   (iii) means for detecting the acoustic wave and providing the location of the gas flow, based on a recorded position and movement of the acoustic wave.

18. The system of claim 17, wherein the hollow-core optical fiber comprises an inner cladding layer surrounding the central core region; and an outer cladding layer surrounding the inner cladding layer.

19. The system of claim 18, wherein the outer cladding layer comprises solid glass.

20. The system of claim 17, wherein the means for detecting the acoustic wave comprises at least one microphone.

* * * * *